United States Patent
Chaussy et al.

(10) Patent No.: US 7,008,372 B2
(45) Date of Patent: Mar. 7, 2006

(54) ARTIFICIAL ENDOSPHINCTER

(75) Inventors: Christian Chaussy, Strasslach (DE); Stefan Thüroff, München (DE); Klaus Schmitt, Remshalden (DE)

(73) Assignee: Willy Rüsch GmbH, Kernen-Rommelshausen ( * ) Notice: Subject to any disclaimer, the term of this patent is extended or adjusted under 35 U.S.C. 154(b) by 240 days.

(21) Appl. No.: 10/717,442

(22) Filed: Nov. 21, 2003

(65) Prior Publication Data

US 2004/0107005 A1 Jun. 3, 2004

(30) Foreign Application Priority Data

Nov. 30, 2002 (DE) .......................................... 102 56 027

(51) Int. Cl.
*A61F 2/02* (2006.01)

(52) U.S. Cl. .......................................... 600/30; 604/246

(58) Field of Classification Search ............. 600/29–32; 604/246, 247; 606/197–198; 623/1.15–1.18, 623/1.2–1.24, 1.3–1.34; 128/DIG. 25; 137/625.28; 251/4, 7, 336, 342
See application file for complete search history.

(56) References Cited

U.S. PATENT DOCUMENTS

| | | | | |
|---|---|---|---|---|
| 4,655,771 A | * | 4/1987 | Wallsten | .................... 623/1.22 |
| 4,968,294 A | | 11/1990 | Salama | |
| 5,078,720 A | * | 1/1992 | Burton et al. | ................ 606/108 |
| 5,800,339 A | | 9/1998 | Salama | |
| 5,954,766 A | | 9/1999 | Zadno-Azizi | |
| 5,971,967 A | * | 10/1999 | Willard | ...................... 604/264 |
| 6,022,312 A | * | 2/2000 | Chaussy et al. | .............. 600/29 |
| 6,162,244 A | | 12/2000 | Braun | |
| 6,488,702 B1 | | 12/2002 | Besselink | |

FOREIGN PATENT DOCUMENTS

| | | |
|---|---|---|
| DE | 295 07 519 | 8/1995 |
| DE | 195 09 464 | 6/1996 |
| WO | WO 98 32 412 | 7/1998 |
| WO | WO 99 13 801 | 3/1999 |

OTHER PUBLICATIONS

Flexmedics, Nitinol . . . The Material of Choice for Safer, More Effective Medical Procedures, 1989.*

* cited by examiner

*Primary Examiner*—John P. Lacyk
(74) *Attorney, Agent, or Firm*—Dr. Paul Vincent

(57) ABSTRACT

In an artificial endosphincter (1) for the urethra, comprising a retaining part (2) and a valve (10) which can be manually actuated by pressure from the outside, the retaining part (2) is formed as self-expanding stent. This permits gentle, simple and safe positioning as well as reliable and simple handling of the artificial endosphincter (1).

20 Claims, 1 Drawing Sheet

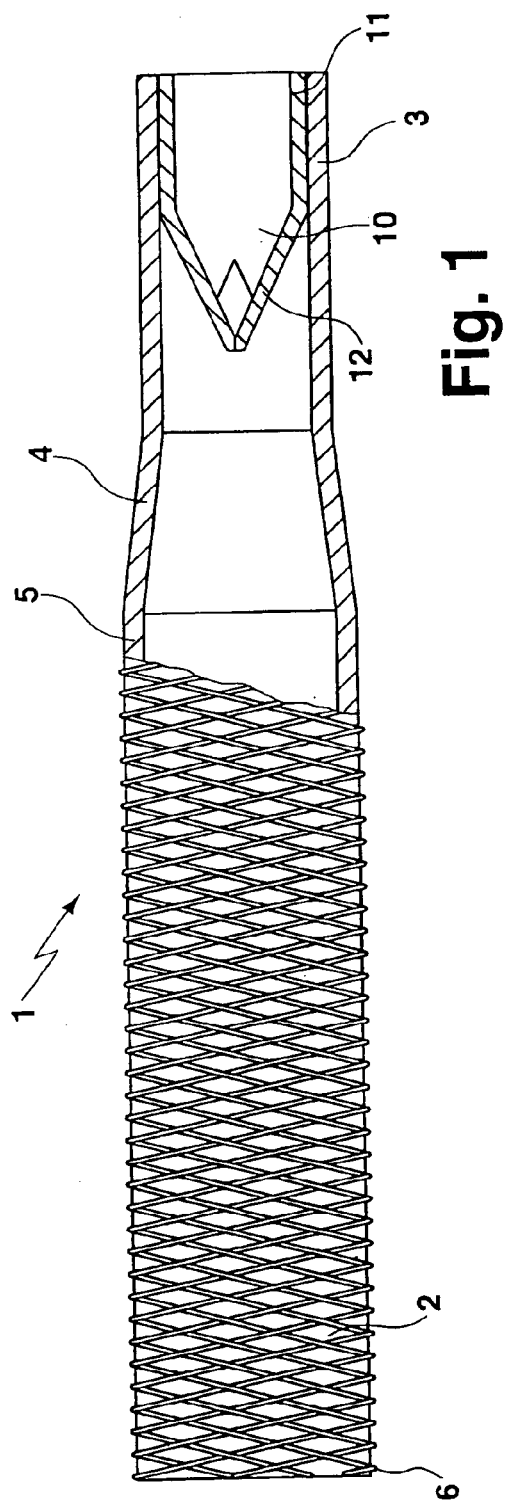
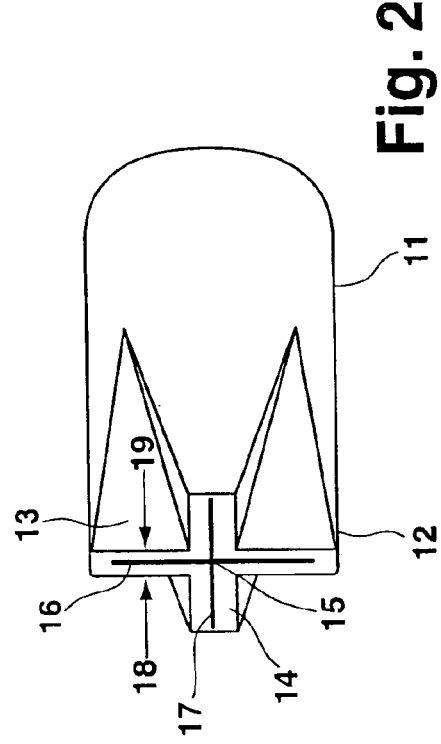
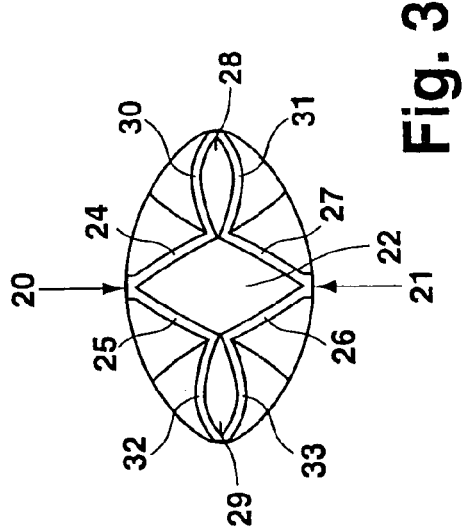

ARTIFICIAL ENDOSPHINCTER

This application claims Paris Convention priority of DE 102 56 027.7 filed Nov. 30, 2002, the complete disclosure of which is hereby incorporated by reference.

BACKGROUND OF THE INVENTION

The invention concerns an artificial endosphincter for the urethra comprising a retaining part and a valve which can be manually actuated by pressure from the outside.

An artificial endosphincter of this type is disclosed e.g. in EP 96 018 05.

Artificial endosphincters are used for incontinency therapy for men after a prostrate resection and for "old incontinent men". The urethra lies between the two cavernous bodies on the lower side of the penis. The urethra is pressed from below by thumb and index finger against the upward lying, parallel cavernous bodies. The pressure on the urethra also exerts pressure on the manually actuatable valve which should thereby open. Since the urethra is surrounded by the cavernous bodies through approximately 270°, the artificial endosphincter must be positioned such that the valve can be opened by a pressure manually built up from the outside through a relatively narrow angular region of the urethra of approximately 90°.

U.S. Pat. No. 6,022,312 discloses an artificial endosphincter whose retaining part has two different diameters, wherein a valve body is mounted to that retaining part section having the smaller diameter. The artificial endosphincter has a holding region between the retaining part having a smaller diameter and the retaining part having a larger diameter. The conventional retaining part is introduced, in an insertion configuration, into a hollow organ and is then expanded by the body temperature. The valve body also comprises two sealing lips which enclose a slitted opening. The sealing lips must be disposed parallel to the actuating direction in the urethra and must therefore be properly oriented when the artificial endosphincter is positioned. If this is not possible, the sealing lips may come to rest transversely or perpendicularly to the actuating direction. In this case, finger pressure can no longer open the valve, rather closes it more tightly.

It is therefore the object of the present invention to further develop an artificial endosphincter of the above-mentioned type such that it can be expanded independently of temperature and/or has a valve which can be opened independently of position.

SUMMARY OF THE INVENTION

This object is achieved in accordance with the invention in that the retaining part is formed as a self-expanding stent.

A self-expanding stent avoids the need for expansion using a balloon or based on increased temperatures. Introduction of the stent is greatly facilitated. For introduction, the stent can be compressed e.g. through extension thereof. After insertion it automatically expands substantially to the shape it had prior to compression. The self-expanding stent is flexible and can follow the curvature of the urethra.

In one preferred embodiment, the sent is a tubular interlacing which is produced from at least one filament. Production of a self-expanding stent with such a tubular interlacing is particularly straightforward.

The inventive artificial endosphincter can preferably be shortened e.g. by simply cutting the stent. Towards this end, the stent has sections without tubular interlacing at which the stent can be easily cut off. This permits individual adjustment and adaptation of the artificial endosphincter to each patient and a relatively short retaining part can be used for incontinence therapy. In case of acute urinary retention or blockage, the uncut retaining part can be used to circumvent the functioning sphincter.

In a preferred embodiment of the invention, the at least one filament has a round cross-section. This is advantageous in that the tissue of the urethra can adapt well to the stent and the tissue is not injured when the stent is inserted and removed. Depending on the application of the stent, it may be advantageous to select a filament with different cross-section, e.g. rectangular, triangular or elliptical.

In a particularly preferred embodiment of the invention, the at least one filament is produced from plastic material or metal. A stent produced from these materials has a type of "shape memory" and therefore displays the so-called "memory effect". Following compression, the tubular interlacing always returns to its expanded, initial state. The tubular interlacing can be compressed to introduce the stent with a small lumen. After introduction into the urethra, the stent automatically expands to produce a large stent lumen for unobstructed urine flow to the valve.

The artificial endosphincter advantageously has X-ray impermeable markings, in particular at its ends. In this way, the position of the artificial endosphincter can be monitored using radiographs. The X-ray impermeable markings may be provided only on the stent.

A cylindrical stent advantageously facilitates removal of the endosphincter in a particularly easy manner, since the stent has no bulge which could impair displacement in the urethra. A cylindrical stent can be compressed to a particularly small size and therefore be inserted without causing significant irritation.

A stent with at least two cylindrical sections of different radii advantageously allows its restoring force to be adjusted to different areas in e.g. the region of the prostrate or of the annular muscle connecting to the bladder. A sufficiently large lumen of the endosphincter can therefore be guaranteed. The stent may have other advantageous shapes, e.g. bulged shapes, and lumen enlargements in sections, in dependence on the application.

In a particularly preferred embodiment, the tubular interlacing has both an inside and outside coating creating a flat inner surface and manifesting the interlacing structure on the outer surface. The flat inner surface permits good flow of urine in the stent and prevents deposits (incrustations). The coating on the outer surface of the stent is preferably thinner than the diameter of the filament such that the structure of the tubular interlacing is maintained and the stent is thereby held stationary in the urethra. In particular, the tubular interlacing surrounds a tube on the surface of which a coating is applied to hold the tubular interlacing on the tube. The coating which holds the tubular interlacing on the tube is preferably made from the same material as the tube. This provides particularly good e.g. material-bonding connection of the two coatings.

In a preferred further development, the tube terminates in a valve receptacle. With this measure, the valve receptacle is held at the retaining part. It is also possible to form the tube and valve receptacle from the same material as one single piece.

When the transition region between valve receptacle and tube is conical, the valve receptacle may have a smaller diameter than the tube. This transition region permits compression of the tube and thereby also of the stent to approximately the diameter of the valve receptacle. Due to this measure, the artificial endosphincter is not damaged during positioning.

In a further development, the transition region is coated by the tubular interlacing. This measure facilitates removal of the artificial endosphincter from the urethra.

When the filaments of the tubular interlacing taper along the transition region towards the valve receptacle, the elasticity and flexibility of the transition region is also maintained at the valve-side end. Formation of a rigid material ring of compressed filaments with equal thickness is thereby avoided.

In a particularly preferred fashion, the tube and valve receptacle are formed in one piece, in particular, from silicone. The one-piece design permits inexpensive production of the endosphincter and simplifies assembly of the endosphincter. Silicone is a highly-flexible material which can be deformed during positioning and automatically assumes its original shape after positioning is completed. In particular, it is important that the valve receptacle returns to its original shape after actuation of the valve and automatic closure thereof following intentional opening.

In a particularly preferred embodiment, the valve is an automatically closing, crossed slotted valve. The use of a crossed slotted valve is highly advantageous in that the valve can be actuated at almost any position in the urethra and the orientation of the artificial endosphincter following positioning in the urethra is unimportant. Inadvertent closing of the valve while exerting pressure on the urethra is not possible and malfunction is nearly impossible.

In a particularly preferred embodiment, the crossed slotted valve has a hollow cylindrical mounting section and a closing section facing the retaining part. The valve is held in the valve receptacle by the hollow-cylindrical mounting section. The mounting section thereby abuts with its outer surface on the inner surface of the valve receptacle. The valve is positively held with the mounting section in the valve receptacle. Since the closing section of the crossed slotted valve faces the retaining part, closing of the crossed slotted valve is facilitated in response to liquid pressure in an axial direction of the artificial endosphincter. The higher the pressure which is exerted on the closing section, the better the valve closes.

In a preferred further development, the crossed slotted valve has pressure receiving surfaces. These pressure receiving surfaces can accept static pressure from four sides, to ensure good closure of the sealing lips.

The crossed slotted valve is advantageously produced from silicone. When the crossed slotted valve and the valve receptacle are produced from the same material, they are uniformly deformed when pressure is exerted on the urethra. Due to the elastic properties of silicone, the valve and the valve receptacle return to their original positions when no pressure is exerted. The crossed slotted valve thereby closes automatically when no radial pressure is exerted on the urethra.

Further features and advantages of the invention can be extracted from the following description of an embodiment of the invention, from the figures of the drawing which show details which are essential to the invention, and from the claims. The individual features can be realized individually or collectively in arbitrary combination in variations of the invention.

The schematic drawing shows one embodiment of the inventive artificial endosphincter which is explained in the following description.

BRIEF DESCRIPTION OF THE DRAWING

FIG. 1 shows a partial longitudinal section through an artificial endosphincter;

FIG. 2 shows a perspective view of a closed valve; and

FIG. 3 shows a front view of an open valve.

DESCRIPTION OF THE PREFERRED EMBODIMENT

The figures are highly schematic to illustrate the essential inventive features. The dimensions in the drawings are only exemplary and are not to be taken to scale.

FIG. 1 shows a partial longitudinal section through an artificial endosphincter 1. The artificial endosphincter 1 has a retaining part 2 which is formed as a stent, a valve receptacle 3, and a transition region 4 joining the valve receptacle 3 to the retaining part 2. The inner diameter of the valve receptacle 3 is smaller than the inner diameter of the retaining part 2. The transition region 4 is conical to compensate for this difference of inner diameters. The artificial endosphincter 1 is tubular, and the tube 5 is covered with a tubular interlacing 6 in the region of the retaining part 2. The tubular interlacing 6 is surrounded by a thin coating (not shown) which holds the tubular interlacing 6 on the tube 5. The layer thickness of the coating is sufficiently thin to maintain the structure of the interlacing 5, to effect secure fixing in the urethra. The retaining part 2 can be extended thereby permitting the size of the inner diameter of the retaining part 2 to approach that of the inner diameter of the valve receptacle 3. The inner surface of the tube 5 is smooth to prevent deposits. The transition region 4 and the valve receptacle 3 have no tubular interlacing. A crossed slotted valve 10 is held in the valve receptacle 3. The crossed slotted valve 10 has a hollow cylindrical mounting section 11 and a closing section 12 facing the retaining part. In the position shown, the crossed slotted valve 10 is closed. Upon radial pressure on the valve receptacle 3, the closing section 12 opens into an aperture through which urine may exit.

FIG. 2 shows a perspective view of the crossed slotted valve 10. The cylindrical mounting section 11 is followed by the closing section 12. Pressure receiving surfaces 13 are provided in the closing section 12 which terminate in sealing lips 14. The crossed slot 15, which is closed in FIG. 2, is disposed between the sealing lips 14. The crossed slot 15 opens at least along one of the lines 16, 17 in response to radial pressure on the crossed slotted valve 10. With the inventive crossed slotted valve 10, it is nearly irrelevant at which location radial pressure is exerted on the crossed slotted valve 10 to open the crossed slot 15. FIG. 2 shows that, when liquid is present at the closing section 12, pressure is exerted on the pressure receiving surfaces 13, e.g. in the direction of the arrows 18, 19. The sealing lips 14 are thereby pressed onto one another with greater force to safely close the crossed slotted valve 10.

FIG. 3 shows a front view of an open valve 10. Radial pressure in the direction of the arrows 20, 21 generates a main opening 22 between the sealing lips 24 to 27 and two side openings 28, 29 between the sealing lips 30, 31 or 32, 33. When radial pressure is removed from the crossed slotted valve 10, it returns to its initial position and the sealing lips close the openings 22, 28, 29.

An artificial endosphincter 1 for the urethra comprises a retaining part 2 and a valve 10 which can be manually actuated from outside through pressure, the retaining part 2 being formed as a self-expanding stent. This permits gentle, simple and safe positioning as well as reliable and simple handling of the artificial endosphincter 1.

We claim:

1. An artificial endosphincter for a urethra, the endosphincter comprising:
a retaining part, structured as a temperature-independent, self-expanding stent; and
a valve which can be manually actuated by external pressure, wherein said valve is a self-closing, crossed slotted valve.

2. The endosphincter of claim 1, wherein said stent comprises a tubular interlacing having at least one filament.

3. The endosphincter of claim 2, wherein said retaining part has at least one section without said tubular interlacing.

4. The endosphincter of claim 2, wherein said at least one filament has a round cross-section.

5. The endosphincter of claim 2, wherein said at least one filament is produced from one of a plastic material and a metal material.

6. The endosphincter of claim 1, further comprising X-ray impermeable markings.

7. The endosphincter of claim 1, wherein said stent is cylindrical.

8. The endosphincter of claim 1, wherein said stent has at least two cylindrical sections of different radii.

9. The endosphincter of claim 2, further comprising an inner coating and an outer coating, wherein said tubular interlacing is disposed between said inner coating and said outer coating, said inner coating having a smooth inner surface and said outer coating having a structure caused by said tabular interlacing.

10. The endosphincter of claim 9, wherein said inner coating is formed as a tube which is surrounded by said tubular interlacing.

11. The endosphincter of claim 10, wherein said tube leads into a valve receptacle.

12. The endosphincter of claim 11, further comprising a conical transition region disposed between said valve receptacle and said tube.

13. The endosphincter of claim 12, wherein said transition region is covered by said tubular interlacing.

14. The endosphincter of claim 13, wherein filaments of said tubular interlacing taper towards said valve receptacle.

15. The endosphincter of claim 11, wherein said tube and said valve receptacle are formed as one piece.

16. The endosphincter of claim 15, wherein said one piece consists essentially of silicone.

17. The endosphincter of claim 1, wherein said crossed slotted valve has a hollow cylindrical mounting section and a closing section facing said retaining part.

18. The endosphincter of claim 1, wherein said crossed slotted valve has pressure receiving surfaces.

19. The endosphincter of claim 18, wherein said pressure receiving surfaces terminate in sealing lips.

20. The endosphincter of claim 13, wherein said valve is a crossed slotted valve consisting essentially of silicone.

* * * * *